United States Patent [19]

Rodriguez

[11] Patent Number: 5,399,759
[45] Date of Patent: Mar. 21, 1995

[54] PROCESS FOR CONDUCTING CHEMICAL REACTIONS WITH FORMALDEHYDE

[75] Inventor: Gilbert Rodriguez, Rodeo, Calif.

[73] Assignee: Imperial Chemical Industries PLC, Millbank, United Kingdom

[21] Appl. No.: 872,775

[22] Filed: Apr. 22, 1992

Related U.S. Application Data

[63] Continuation-in-part of Ser. No. 680,468, Apr. 4, 1991, abandoned.

[51] Int. Cl.$^6$ ............................................. C07C 233/12
[52] U.S. Cl. .................................... 564/214; 564/276; 564/277
[58] Field of Search ............... 564/277, 214, 276, 271, 564/143, 202, 203

[56] References Cited

U.S. PATENT DOCUMENTS

| | | | |
|---|---|---|---|
| 1,417,970 | 5/1922 | Cadwell | 260/562 R |
| 1,418,824 | 6/1922 | Naylor | 260/562 R |
| 2,088,143 | 7/1937 | Sutter | 260/130 |
| 3,207,813 | 9/1965 | Harvey | 260/834 |
| 3,630,716 | 12/1971 | Olin | 71/118 |
| 3,637,847 | 1/1972 | Olin | 260/562 B |
| 3,835,191 | 9/1974 | Wagner et al. | 260/566 R |
| 3,976,471 | 8/1976 | Richter et al. | 71/105 |
| 4,097,262 | 6/1978 | Cheng | 71/90 |
| 4,261,733 | 4/1981 | Chupp | 71/118 |
| 4,319,917 | 3/1982 | Grove | 71/105 |
| 4,399,306 | 8/1983 | Domjan et al. | 564/214 |
| 4,491,672 | 1/1985 | Richarz et al. | 564/271 |

FOREIGN PATENT DOCUMENTS

| | | |
|---|---|---|
| 64173 | 3/1978 | Romania . |
| 1078072 | 8/1967 | United Kingdom . |
| 1546029 | 5/1979 | United Kingdom . |

OTHER PUBLICATIONS

Chupp et al., J. Org. Chem. 34, 1192 (1969).
Moon et al., J. Korean Chemical Society, vol. 27, p. 157. (1983).
Barluenga et al., J. Chem. Soc., Chem. Commun., p. 1109 (1983).
Barluenga et al., J. Chem. Soc., Perkin Trans., vol. I, p. 1631 (1988).
J. F. Walker *Formaldehyde* 3rd Ed. Reinhold Pub. Corp. 1964 pp. 151–153, 264–267.

Primary Examiner—Glennon H. Hollrah
Assistant Examiner—Brian M. Burn
Attorney, Agent, or Firm—Joel G. Ackerman

[57] ABSTRACT

A formaldehyde reactant is provided to a chemical process or reaction, in the form of a formaldehyde-alcohol complex, by contacting paraformaldehyde with from about 0.25 to about 3 mole equivalents of an aliphatic alcohol in the presence of a catalytic amount of a base. In a preferred embodiment the chemical process is a process for the production of an aromatic azomethine by reaction of an aniline with formaldehyde. The azomethine may then be used to produce a haloacetanilide.

18 Claims, No Drawings

PROCESS FOR CONDUCTING CHEMICAL REACTIONS WITH FORMALDEHYDE

CROSS-REFERENCE TO RELATED APPLICATION

This application is a continuation-in-part of application Ser. No. 07/680,468, filed Apr. 4, 1991, now abandoned.

BACKGROUND AND PRIOR ART

This invention relates to the use of formaldehyde reactants in chemical processes or reactions, particularly those conducted in the presence of, or which generate some, water. In a preferred embodiment, this invention relates to a process for production of azomethines by reaction of an aniline with formaldehyde, and also to a process for production of haloacetanilides from anilines by reaction of the latter with formaldehyde to form azomethines, reaction of the azomethine with an acyl halide and, if an N,N-disubstituted haloacetanilide is the ultimate product, further reaction with an appropriate agent, for instance, an alcohol.

Processes of this general type, resulting in the formation of haloacetanilides are described, for example, in U.S. Pat. Nos. 3,630,716, 3,637,847 and 4,097,262. In all three patents, the first step involves the reaction of an optionally substituted aniline with formaldehyde to produce an azomethine according to the general reaction

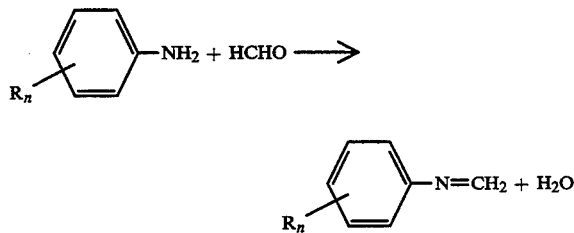

In such processes, the physical state and nature of the formaldehyde can pose handling and recovery problems. Formaldehyde is generally commercially available in the form of either an aqueous solution, such as formalin, or solid paraformaldehyde. Formalin, being a liquid, is easier to handle than solids but the large amounts of water and alcohol associated with formalin pose disposal problems. Paraformaldehyde, being a polymeric solid, is less reactive and can form polymeric impurities. Furthermore, if removal of unreacted paraformaldehyde from the reaction mixture is required, filtration or sublimation at elevated temperatures would be necessary. These require expensive and high maintenance equipment on the one hand, or can produce degradation of the desired product (due to elevated temperature), as well as fouling of condenser tubes and other apparatus by deposited paraformaldehyde. Additionally, formaldehyde related impurities can be carried through the process, resulting in impurities in the ultimate product.

U.S. Pat. Nos. 3,630,716 and 3,637,847 describe (examples 36–47 of each) reaction of various anilines with formaldehyde used in the form of the trimer trioxymethylene. In some of these examples, the reaction is conducted in the presence of a small amount of trimethylamine in methanol, while in other examples, no trimethylamine or methanol was present. This appears to be explained by the comments in British Patent 1,078,072, that "basic catalysts" such as trimethylamine, may be used to neutralize any formic acid present in the formaldehyde. The patent points out, however, that the reaction will proceed in the absence of a catalyst and this is demonstrated by the presence of other examples in the two U.S. patents in which no catalyst was used.

Two more recent patents provide expedients to deal with the problems of formaldehyde handling referred to above.

U.S. Pat. No. 4,399,306 describes an overall process for production of N-alkoxyalkyl haloacetanilides involving a number of expedients, some of which are directed to the problems of formaldehyde handling. The patent points out that in the azomethine production step, formaldehyde is generally used in excess; that a stoichiometric amount of formaldehyde will not result in complete reaction of the aniline. The patent further refers to the problems of formaldehyde in the reaction products, including its appearance as an impurity in the azomethine as well as in the final haloacetanilide product. This patent proposes a process which uses a stoichiometric amount of an aqueous formaldehyde solution in an apolar solvent followed by dehydration to produce the azomethine derivative. The aqueous formaldehyde solution is removed at a temperature of 80° C. to 140° C. However, as pointed out above, the aqueous formaldehyde solution so removed must be disposed of.

U.S. Pat. No. 4,491,672 of Richarz et al. purports to solve the problems arising from use of formaldehyde by carrying out the production of the azomethine without a solvent, followed by distillation of the water at a pressure of less than 500 mbar, the distillation being carried out in the presence of an alcohol having a boiling point below 160° C. In this process the formaldehyde is used in the form of a gas or a compound which "forms formaldehyde under the reaction conditions, e.g. paraformaldehyde or trioxane". Paraformaldehyde appears to be preferred.

The present invention, however, provides formaldehyde in a form which is more reactive and more usable, and which additionally can be recovered for reuse in the process.

SUMMARY OF THE INVENTION

In brief, this invention relates generally to a means for providing a formaldehyde reactant to a chemical process or reaction, comprising contacting paraformaldehyde with from about 0.25 to about 3 mole equivalent of an aliphatic alcohol, in the presence of a catalytic amount of a base, and providing the product of said contacting to the process or reaction as a formaldehyde reactant.

In a more specific embodiment, this invention comprises a process for the production of an aromatic azomethine by reaction of an aniline with formaldehyde, in which the formaldehyde is provided by (a) contacting paraformaldehyde with from about 0.25 to about 3 mole equivalent of an aliphatic alcohol in the presence of a catalytic amount of a base; and (b) contacting the product of step (a) with the aniline to form the azomethine.

DETAILED DESCRIPTION OF THE INVENTION

According to the general aspect of this invention, a reactive form of formaldehyde is provided to a chemical process or reaction in which formaldehyde is a reactant, and preferably in which water is present or is generated. The water may be present in up to 300 mole percent. The formaldehyde is provided to the process or reaction in the form of a product resulting from contact of solid paraformaldehyde with from about 0.25 to about 3 mole equivalent of an aliphatic alcohol (as defined below) in the presence of a catalytic amount of a base. For purposes of convenience, the product of this contacting step will be referred to as a "formaldehyde-alcohol complex", though other terminology may be used.

In the contacting step, solid paraformaldehyde is mixed with a lower aliphatic alcohol together with a catalytic amount of a base, which serves to catalyze depolymerization of the paraformaldehyde with the alcohol. The alcohol which is used in this process is a lower aliphatic alcohol containing a straight or branched chain alkyl group having from 1 to 4, preferably from 1 to 2, carbon atoms. In the process of this invention, the alcohol is utilized in an amount of-from about 0.25 to about 3 mole equivalent, preferably from about 0.35 to about 2 mole equivalent, most preferably from about 0.35 to about 1 mole equivalent, with respect to formaldehyde.

Preparation of the formaldehyde-alcohol complex is preferably carried out at a temperature of about 85°-95° C. An inert solvent, for instance, an aromatic solvent such as xylene, may also be present, but is not required. It has been found that formaldehyde-alcohol complexes so formed may be stored for periods of up to a year, or even more, and remain stable. Therefore, it is possible to prepare a substantial amount of such a complex at one time, which may then be used over time as needed.

The base utilized may be an organic or inorganic base such as an alkali metal hydroxide, alkoxide, carbonate or oxide or a tertiary amine. Tertiary amines are preferred. Typical catalysts for this technique include sodium hydroxide, potassium hydroxide, sodium methoxide, trialkylamines such as trimethylamine, triethylamine, and tri-n-butylamine, and heterocyclic amines including pyridine, N-alkylpiperidines and -pyrrolidines (for example, N-ethylpiperidine and N-methylpyrrolidines), tetraalkylguanidines and fused bicyclic amines such as 1,8-diazabicyclo(5.4.0)undec-7-ene and 1,5-diazabicyclo(4.3.0)non-5-ene. The basic catalyst is generally used in an amount of from about 0.01 to about 1, preferably from 0.01 to about 0.05 mole equivalent, based on formaldehyde.

Without being bound by any theory, it is believed that the product formed between the paraformaldehyde and aliphatic alcohol is a complex which may be or include a hemiacetal or diacetal of formaldehyde. Preparation of such hemiacetals is suggested in the text Formaldehyde by J. Frederick Walker, for example, at page 202. In any event, irrespective of the physical or chemical form of the formaldehyde, it is found that by the use of this technique, the reaction between aniline and formaldehyde proceeds almost instantaneously, as opposed to prior art techniques in which reaction is much slower. Additionally, only a small excess of formaldehyde is required as opposed again to prior art techniques in which formaldehyde was used in substantial excess, for example, in U.S. Pat. Nos. 4,399,306 and 4,491,672.

In a preferred embodiment, this invention relates to using such an alcohol-formaldehyde complex in a process to produce an aromatic azomethine according to the reaction:

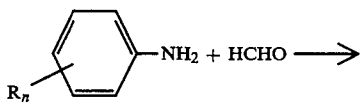

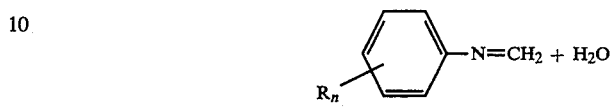

In this process, an optionally substituted aniline is reacted with formaldehyde, producing an azomethine and water.

The aniline in general has the formula

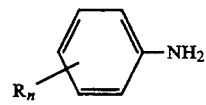

in which R represents hydrogen or one or more substituents which are relatively non-reactive with formaldehyde, particularly alkyl, alkoxy, or halogen; n is generally at a value of from 0 to 5, and is preferably 0, 1, 2 or 3. Herbicidal anilides or haloacetanilides are often prepared from anilines having one or more such substituents in the ortho position(s). Some typical starting anilines for this process, when used to ultimately prepare herbicidal anilides or haloacetanilides, include 2,6-dimethylaniline, 2,6-diethylaniline, 2-methyl,6-ethylaniline, 2-methyl,6-tertiarybutylaniline, 2-tertiarybutyl,6-haloanilines, 2,4-dimethylaniline, 2-tertiarybutyl-5,6-dimethylaniline, 2,6-dimethyl-3,4,5-trichloroaniline, 2-methylaniline, 2-ethylaniline, 2-methoxyaniline, 2-ethoxyaniline, and other anilines mentioned in the patents referred to in the "Background and Prior Art" section above.

In the case in which the process to produce azomethines is the first step in a multi-step process to produce herbicidal haloacetanilides, the final product (typically termed an α-haloacetanilide, or more commonly α-chloroacetanilide) has the general formula

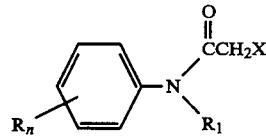

in which R and n are as described above; X is a halogen, usually chloro or bromo and most usually chloro, and $R_1$ is any of a number of substituents which have been described as components of herbicidal compounds, the most common of which tend to be various alkyl and alkoxyalkyl groups. Other substituents are described, for instance, in U.S. Pat. No. 4,097,262.

As is known in the art, the reaction of the aniline and formaldehyde is generally carried out in a hydrocarbon solvent, which forms an azeotrope with water at the reflux temperature of the solvent. Typical solvents include aromatic solvents such as benzene, toluene, and xylene, and aliphatic and cylcoaliphatic solvents such as n-hexane, n-heptane and cyclohexane. Depending on the solvent, the reflux temperature of the reaction will range from about 80° C. to about 140° C. Preferred reaction temperatures are between about 80° C. and 100° C., with the solvent and/or pressure being appropriately chosen.

The process for forming an azomethine according to this invention can be carried out in one or two stages or reactors.

In the two-stage embodiment, the formaldehyde-alcohol complex is produced by first forming the formaldehyde-alcohol complex, by combining the paraformaldehyde, alcohol, and base catalyst in an appropriate apparatus and then contacting the resulting product with the aniline reactant in a solvent. This two-stage embodiment can be carried out in two separate pieces of apparatus, one for the production of the formaldehyde-alcohol complex and the other for the conduct of the reaction of formaldehyde (in the form of the complex) with the aniline. Alternatively, the two-stage process can be carried out in a single piece of apparatus, with the formaldehyde-alcohol complex first being produced, and the aniline and solvent thereafter added, and the temperature raised to the reflux temperature of the solvent.

In the single stage embodiment, all materials—the paraformaldehyde, the alcohol, the base catalyst, the aniline, and the solvent—are mixed in a single reactor at a temperature below the reaction temperature. The reactor temperature is then raised to that appropriate for the reaction. During the time when the temperature is being raised, the paraformaldehyde reacts with the alcohol and base catalyst to form the formaldehyde-alcohol complex, and once the appropriate reaction temperature is reached, the complex and the aniline react to form the azomethine product.

One advantage of the use of the present process over the prior art is that in general the reaction to produce the azomethine is run under reflux. In the prior art techniques utilizing solid paraformaldehyde, it had been necessary to heat the paraformaldehyde, which would sublime and deposit on the condenser. The present technique avoids this plugging problem. The formaldehyde or the formaldehyde-alcohol complex will condense and reform as the formaldehyde-alcohol complex, which is a liquid.

Another advantage of the process as practiced using this invention is that the formaldehyde-alcohol complex will react almost instantaneously with the aniline.

In general, the reaction of the formaldehyde reactant with aniline to produce the azomethine is carried out as known in the art. The presence of some water in the reaction system (up to about a few mole equivalents with respect to the aniline) at the start of the process is permissible and in fact may even assist in the initiation of the reaction. Also, the presence of water is believed to aid in minimizing the production of a bisalkoxymethylaniline impurity.

Of course, water is a product of the formaldehyde-aniline reaction. It is removed from the reaction products by azeotropic distillation. The formaldehyde and alcohol, and/or formaldehyde-alcohol complex are also removed by distillation. Preferably in the present process, the distillation is conducted continually during most of the course of the reaction, beginning shortly after the reaction itself commences. The water is removed with the solvent. The distillation is azeotropic or zeotropic, depending on the solvent. The progress of the reaction can be followed by gas chromatographic analysis or other monitoring technique such as analyzing a sample of condensate for moisture content. Gas chromatographic analysis can be utilized to monitor the reaction product for the azomethine content, and the reaction is generally considered complete when the azomethine content (expressed as a ratio of azomethine to unreacted aniline) reaches about 98% (or alternatively when residual aniline content is less than 2%). If analyzing for moisture content, the reaction is considered complete when the moisture content of the distillate is less than 150 ppm.

After the reaction is complete, the product is cooled to ambient temperature.

A further advantage of the use of formaldehyde-alcohol complexes, both in general and in the azomethine process, is that the complex is easily removed from the reaction mixture by evaporation. The condensate recovered from the azeotropic distillation contains unreacted formaldehyde, alcohol, solvent, water, and base (if an organic base such as a tertiary amine was used). This condensate can be separated into organic and aqueous phases, with most of the formaldehyde contained in the aqueous phase. The aqueous phase may be treated to remove formaldehyde and/or alcohol, if necessary, is properly further treated if need be, and discarded. The organic phase can be reused to dissolve more paraformaldehyde for the next run.

In a process for production of haloacetanilides through the azomethine, the reaction product from the azomethine process is cooled to the appropriate temperature and contacted in the conventional manner with a haloacetylating agent, usually chloroacetyl chloride, in an appropriate solvent (which may be an aromatic or aliphatic hydrocarbon solvent such as those used for the azomethine process). The product in this reaction is a 2- or α-halo (preferably chloro) N-halomethyl (preferably chloromethyl) acetanilide which has the formula

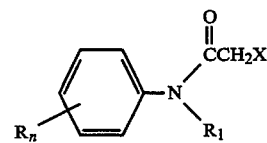

in which X is halo (usually chloro or bromo) and $R_1$ is halomethyl (chloromethyl or bromomethyl). Haloacetanilides of this type are described as herbicides in U.S. Pat. Nos. 3,630,716 and 3,637,847.

If desired, these haloacetanilides can be further reacted with an aliphatic alcohol to produce an N-alkoxyalkyl-α-haloacetanilide, as shown for example in U.S. Pat. No. 4,399,306.

It has been found that the use of the present invention in the process for producing the azomethine can yield to improved results in terms of either product purity or yield, or possibly both, of the final haloacetanilide product, particularly when a three-step process is utilized to produce an N-alkoxyalkyl-α-chloroacetanilide.

In the conventional processes for production of haloacetanilides from anilines, the several steps are usually carried out in separate reactors or apparatus, with removal, cooling and purification of the reaction product after each stage. If preferable or convenient, haloacetanilides, including N-alkoxyalkyl-α-haloacetanilides, can be similarly produced from the azomethine-containing reaction products obtained with the present invention. However, it has also been found that the use of this invention can produce an azomethine-containing reaction product of sufficient quality that subsequent steps can be carried out in the same reaction apparatus without need for purification of the product between steps. This permits a "one-pot" type of operation of the complete haloacetanilide process.

Such a one-pot process can have economic and environmental advantages. There is a substantial reduction in capital costs. Fewer washing steps are needed, reducing the amount of liquid waste. Ammonium chloride solids recovered from the final step are relatively pure and may be used (or sold) for the purposes such as electroplating, explosives manufacture, etc.

The following represents examples of the use of the process of this invention:

EXAMPLE I

This example represents the conduct of the azomethine process in a two-step fashion, in which the formaldehyde reactant is first prepared and is then combined with the aniline reactant.

- A) Production of the formaldehyde reactant. In a reactor were charged 3.0 mole paraformaldehyde, 3.0 mole ethanol, 0.01 mole triethylamine, 1.0 mole xylene and 0.5 moles water. The mixture was then heated to 85°–90° C. and agitated until the solution was clear.
- B) In a reactor were placed 1 mole of 2-methyl,6-ethylaniline and 2 moles of xylene. The contents of the reactor were then heated to about 90° C.

The reaction was allowed to proceed with azeotropic distillation under atmospheric pressure at a temperature of about 95° C., ranging up to 126° C. The reaction mixture was sparged with nitrogen during the distillation. The formaldehyde-ethanol complex was introduced slowly during the azeotropic distillation in 5 aliquots of about 0.5 mole each. The reaction was monitored during this time by gas chromatographic analysis for area percent. This was carried out by removing a sample of the reaction mixture and adding two drops of it to about four drops of chloroacetyl chloride and about 3 ml of chloroform to produce the N-chloromethyl-α-chloroacetanilide derivative. The resulting mixture was injected into a gas chromatograph and the area % concentration ratio of this derivative to the corresponding haloacetanilide lacking the N-chloromethyl group calculated. This anilide forms as a result of the reaction of the chloroacetyl chloride with unreacted aniline. The reaction product was light amber colored. Analysis of the N-chloromethyl derivative as above gave 96–97 area % of the N-chloromethyl derivative (corresponding to the azomethine) and 2–3 area % corresponding to the starting aniline.

EXAMPLE II

This example illustrates conduct of a three-step process to produce an N-alkoxyalkyl α-chloroacetanilide and also shows use of a formaldehyde-alcohol complex which had been prepared, and then stored for more than one year.

A) Preparation of the Formaldehyde-Ethanol Complex Solution

In a reactor equipped with an agitator, a condenser, and heating mantle was added 20 moles paraformaldehyde, 20 moles of ethanol and 0.4 moles of triethylamine. The mixture was slowly heated under atmospheric pressure to reflux, which began at about 90° C. until a clear solution was formed. The formaldehyde-ethanol complex was relatively clear with no precipitation of solids on being stored for more than a year.

B) Preparation of Azomethine with Formaldehyde-Ethanol Complex Solutions that had been stored for over a year In a reactor equipped with an agitator, a condenser, heating mantle, dropping funnel and a condensate receiving flask was charged 474 g (6 moles formaldehyde) of a year-old formaldehyde-ethanol complex solution prepared as above, and 1696 g (16 moles) of xylene. The mixture was heated to about 90° C. and 550 g (4.0 moles) 2-methyl-6-ethylaniline was gradually added to the xylene-complex mixture. The mixture was allowed to reflux while the aniline was being added. When all the aniline was added, the reactor was insulated and the azeotropic distillation began under atmospheric pressure. The temperature of the reaction mixture was allowed to increase to about 125° C. The distillation was then continued under vacuum. The progress of the reaction was monitored by the gas chromatography method discussed in Example I. The reaction was complete within two hours after distillation began. About 1200 ml overhead distillate was recovered. The reaction gave an aniline to azomethine conversion of about 98.4 by area % analysis.

C) Preparation of the N-Chloromethyl-α-Chloroacetanilide Intermediate

The azomethine intermediate obtained above was cooled to about 80° to 90° C. to it, over 30 minutes, was added a solution containing 484 g (4.2 moles) of chloroacetyl chloride and 424 g (4.0 moles) of xylene. This reaction gave a 96.7% conversion of the azomethine to the N-chloromethyl-α-chloroacetanilide intermediate by gas chromatographic area % analysis.

D) Preparation of 2-Methyl-6-Ethyl-N-Ethoxymethyl-2-Chloroacetanilide

About 2208 g (48 moles) of anhydrous ethanol was added to the reaction mixture containing the N-chloromethyl-α-chloroacetanilide intermediate. The addition of ethanol to the haloacetanilide mixture was done over 40 minutes at temperatures ranging from 45°–84° C. At the end of the ethanol addition, about 66.3 g (3.9 moles) of gaseous ammonia was introduced to the reaction mixture through a dip tube at about 50°–60° C. When the pH of the reaction mixture was about 8–9, the addition of ammonia was stopped and the reaction was considered complete. This reaction gave a 98.6% conversion of the haloacetanilide intermediate to the N-ethoxymethyl-2-chloroacetanilide.

The reaction mixture was then filtered to remove the ammonia chloride solids. The filter cake was rinsed with small amounts of xylene to remove residual product. The clear filtrate was recovered and washed witch about 800 ml of 0.2% HCl solution. The mixture was phase separated in a separatory funnel and the organic phase was stripped at 95° C. for about two hours. The final product contained 95.1 wt. % pure desired chloroacetanilide with about 1.0 wt. % of the non-chloromethylated haloacetanilide impurity.

EXAMPLE III

This example illustrates the preparation of formaldehyde/alcohol complex and production of an azomethine in a single reactor.

In a flask equipped with an agitator, a condenser, and a condensate receiving flask, were placed the following materials, sequentially:

Paraformaldehyde (91% pure, 52.8 g, 1.60 moles)

Ethanol (2B, 36.8 g, 0.80 moles)
Triethylamine (3.1 g, 0.03 mole)
Xylene (850 g, 8.0 moles)
2-methyl-6-ethylamine (98% pure, 138 g, 1 mole)

The reactor was insulated and then heated slowly under atmospheric pressure to reflux, which began at about 90° C. The mixture was held under refluxing conditions for about 15 minutes, and then azeotropically dried by collecting the distillate in the condensate receiver and allowing the temperature to rise. The atmospheric distillation was continued until the temperature reached 115° C. and thereafter under vacuum. The temperature was maintained at about 115° C. and the reactor pressure was reduced gradually to 300–320 mmHg.

After completion, the product was cooled to ambient temperature. This product contained about 4.3 moles xylene, weighed 600 g, and had a content of the desired azomethine of about 140 g. The total volume of distillate collected was about 560 ml; of this, about 49 ml was aqueous.

EXAMPLE IV

This example illustrates the use of the invention in conducting the "one-pot" process for production of 2-methyl-6-ethyl-N-ethoxymethyl-2-chloroacetanilide from 2-methyl-6-ethyl aniline in a single reactor.

A) Preparation of the Aromatic Azomethine Intermediate

In a reactor equipped with an agitator, a condenser, heating mantle, dropping funnel and a condensate receiving flask, was placed 95 g (1.2 moles) of formaldehyde-ethanol complex solution that had been previously prepared as in Example I, and 680 g of xylene (6.4 moles). The mixture was heated to about 95° C.

Then, 110 g (0.8 mole) of 2-methyl-6-ethylamine was added to the formaldehyde complex-xylene mixture at about 95° C., over 20–30 minutes. The reaction mixture was allowed to reflux for a few minutes. Then, azeotropic distillation was allowed to proceed under atmospheric pressure until the temperature reached 120° C. At this temperature, the distillation was continued under vacuum (maximum about 250 mm Hg abs.) until the reaction was done. The overhead distillate, including the portion collected from atmospheric distillation, was 488 g (600 ml). It had 46 g of an aqueous phase and 442 g of organic. The moisture content of the last portion of the distillate was about 100 ppm.

B) Production of the N-Chloromethyl-α-Chloroacetanilide Intermediate

The reaction mixture containing the azomethine was cooled to about 70° C. A solution containing 97 g (0.84 moles) of chloroacetyl chloride in 130 g (1.2 moles) xylene was then added slowly to the azomethine mixture. The temperature of the reaction mixture was maintained at about 70° C. until all the chloroacetyl chloride was added. At the end of the addition, the reaction was considered complete. The purity of N-chloromethyl-chloroacetanilide intermediate was 98.9% and of the non-chloromethylated haloacetanilide impurity, 1.06% as determined by gas chromatography area %.

C) Production of the 2-Methyl-6-Ethyl-N-Ethoxymethyl-2-Chloroacetanilide Product The reaction mixture with the N-chloromethyl-α-chloroacetanilide intermediate was cooled to about 50° C. Then gradually there was added 442 g (9.6 moles) anhydrous ethanol. Throughout the ethanol addition, the temperature of the reaction mixture was kept between 45° to 60° C. At the end of ethanol addition, gaseous ammonia was introduced to the reaction mixture through a diptube to neutralize the mixture to a pH of 8–9. At this point, the reaction mixture formed a slurry and was considered complete. A sample of the final reaction mixture showed 99.4% 2-methyl-6-ethyl-N-ethoxymethyl-2-chloroacetanilide with 0.6% non-chloromethylated haloacetanilide impurity by gas chromatography area % analysis.

The slurry was filtered to remove the ammonium chloride solids. A white filter cake weighing about 114 g (wet) was recovered. The filtrate was a clear light amber solution and was stripped of xylene and ethanol at about 95° C. under full vacuum for about two hours. This reaction produced a 96.6 wt. % pure 2-methyl-6-ethyl-N-ethoxymethyl-2-chloroacetanilide with 0.6 wt. % haloacetanilide impurity. The yield was estimated to be 87.3% of the desired product based on 2-methyl-6-ethylamine.

What is claimed is:

1. In a process for production of an aromatic azomethine by reaction of an aniline with formaldehyde, the step of providing the formaldehyde in the form of a product produced by contacting paraformaldehyde with from about 0.25 to about 3 mole equivalents of an aliphatic alcohol having from 1 to 4 carbon atoms in the presence of a catalytic amount of a base.

2. A process according to claim 1 in which the paraformaldehyde is contacted with from about 0.35 to about 2 mole equivalents of the alcohol.

3. A process according to claim 2 in which the paraformaldehyde is contacted with from about 0.35 to about 1 mole equivalents of the alcohol.

4. A process according to claim 1 in which the base is a tertiary amine.

5. A process according to claim 4 in which the base is a trialkylamine.

6. A process according to claim 1 in which the alcohol is a monohydric aliphatic alcohol having from 1 to 2 carbon atoms.

7. A process according to claim 1 in which the aniline has the formula

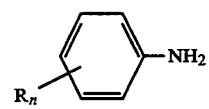

in which R is one or more of alkyl, alkoxy, or halogen and n is an integer of from 1 to 5.

8. A process according to claim 7 in which $R_n$ is 2,6-dimethyl; 2,6-diethyl; 2-methyl,6-ethyl; 2-methyl; 2-ethyl; 2-methoxy or 2-ethoxy.

9. A process according to claim 1 in which the reaction of aniline and formaldehyde is conducted in the presence of an aliphatic, cycloaliphatic, or aromatic hydrocarbon solvent which forms an azeotrope with water.

10. A process according to claim 9 in which the paraformaldehyde is first contacted with the alcohol and catalytic amount of base, and the resulting product is then mixed with the aniline and solvent.

11. A process according to claim 1 in which the paraformaldehyde, alcohol, base and aniline are mixed and the resulting mixture is heated to the reaction temperature.

12. A process according to claim 9 in which the paraformaldehyde, alcohol, base, aniline and solvent are mixed and the resulting mixture is then heated to the reaction temperature.

13. A process according to claim 1, carried out with continual azeotropic distillation of the water of reaction.

14. A process according to claim 13 in which a condensate containing water, solvent, formaldehyde, and alcohol is recovered from the distillation, the condensate is separated into aqueous and organic phase, and the organic phase is contacted with paraformaldehyde to provide formaldehyde reactant to a subsequent conducting of the aniline-formaldehyde reaction.

15. A process according to claim 1 further comprising reacting the azomethine with a haloacetyl halide to produce an N-halomethyl-α-haloacetanilide.

16. A process according to claim 15 further comprising reacting the N-halomethyl-α-haloacetanilide with an aliphatic alcohol to produce an N-alkoxyalkyl-α-haloacetanilide.

17. A process according to claim 16 in which all reactions are conducted in the same apparatus, without removal of reaction products after each step.

18. A process according to claim 16 in which the N-alkoxyalkyl-α-haloacetanilide is 2'-methyl-6'-ethyl-N-ethoxy-methyl-2-chloroacetanilide.

* * * * *